(12) United States Patent
Baxter et al.

(10) Patent No.: US 8,740,960 B2
(45) Date of Patent: **\*Jun. 3, 2014**

(54) DEVICE AND METHOD FOR THE REDUCTION OF PAIN ASSOCIATED WITH NEEDLE STICKS

(75) Inventors: Amy L. Baxter, Atlanta, GA (US); Louis A. Calderon, Atlanta, GA (US)

(73) Assignee: MMJ Labs, LLC, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/426,330

(22) Filed: Mar. 21, 2012

(65) Prior Publication Data

US 2012/0179099 A1    Jul. 12, 2012

Related U.S. Application Data

(63) Continuation of application No. 11/538,718, filed on Oct. 4, 2006, now Pat. No. 8,147,533.

(51) Int. Cl.
*A61F 7/00* (2006.01)
(52) U.S. Cl.
USPC ............... 607/108; 607/96; 601/46; 128/898
(58) Field of Classification Search
USPC ........... 607/96, 108–111; 601/46; 604/21, 22; 128/898
See application file for complete search history.

(56) References Cited

U.S. PATENT DOCUMENTS

| | | | |
|---|---|---|---|
| 3,140,709 A | 7/1964 | Weisz | |
| 3,620,209 A * | 11/1971 | Kravitz | 601/79 |
| 4,082,918 A | 4/1978 | Chang et al. | |
| 4,553,534 A | 11/1985 | Stiegler | |
| 4,676,247 A * | 6/1987 | Van Cleve | 607/112 |
| 5,148,804 A * | 9/1992 | Hill et al. | 607/108 |
| 5,179,944 A | 1/1993 | McSymytz | |
| 5,289,438 A | 2/1994 | Gall | |
| 5,304,112 A | 4/1994 | Mrklas et al. | |
| 5,327,886 A | 7/1994 | Chiu | |
| 5,391,198 A | 2/1995 | Cheney, III et al. | |
| 5,400,617 A * | 3/1995 | Ragonesi et al. | 62/530 |
| 5,447,531 A | 9/1995 | Wood | |
| 5,718,336 A | 2/1998 | Haarlander | |
| 5,855,623 A | 1/1999 | English et al. | |
| 6,023,932 A * | 2/2000 | Johnston | 62/3.5 |
| 6,187,031 B1 | 2/2001 | Douglas | |
| 6,231,531 B1 | 5/2001 | Lum et al. | |

(Continued)

FOREIGN PATENT DOCUMENTS

WO    WO-2006/034324 A2    3/2006
WO    WO-2006/124329 A1    11/2006

OTHER PUBLICATIONS

Lancet article "Vibration Therapy for Pain," The Lancet, 1992, Jun. 20; 339(8808):1513-4.*

(Continued)

*Primary Examiner* — Ahmed Farah
(74) *Attorney, Agent, or Firm* — Ballard Spahr LLP

(57) ABSTRACT

A device that is used to reduce the pain of a needle stick to a person, the device having a casing containing a vibratory device and a temperature reducing device, and a method for using the device to reduce the pain of a needle stick by applying both thermal and vibration analgesia to a subject during a needle stick.

20 Claims, 6 Drawing Sheets

(56) References Cited

U.S. PATENT DOCUMENTS

| | | | |
|---|---|---|---|
| 6,234,986 B1 | 5/2001 | Raffo et al. | |
| 6,277,085 B1 | 8/2001 | Flynn | |
| 6,554,787 B1* | 4/2003 | Griffin et al. | 602/74 |
| 6,641,522 B2 | 11/2003 | August | |
| 8,147,533 B2* | 4/2012 | Baxter et al. | 607/108 |
| 2001/0007952 A1 | 7/2001 | Shimizu | |
| 2003/0009168 A1 | 1/2003 | Beal et al. | |
| 2006/0015062 A1 | 1/2006 | Kahen | |
| 2006/0121423 A1 | 6/2006 | Hutchison | |
| 2006/0178715 A1 | 8/2006 | Ahn et al. | |
| 2007/0100262 A1 | 5/2007 | Simos et al. | |
| 2008/0086063 A1* | 4/2008 | Baxter et al. | 601/46 |
| 2008/0086187 A1 | 4/2008 | Baxter et al. | |
| 2008/0255483 A1 | 10/2008 | Goldberg | |
| 2009/0143689 A1 | 6/2009 | Berry et al. | |
| 2009/0151737 A1 | 6/2009 | Baxter | |

OTHER PUBLICATIONS

"Vibration Therapy for Pain," The Lancet, 1992, Jun. 20; 339(8808):1513-4.*
Smith et al., "Vibration anesthesia: a noninvasive method of reducing discomfort prior to dermatologic procedures," Dermatology Online Journal, 2004, 10(2):1.*
Final Office Action issued by USPTO on Sep. 23, 2011 for U.S. Appl. No. 11/867,630, filed Oct. 4, 2007 (Inventor—Baxter et al.; pp. 1-10).
Response to Non-Final Office Action filed by Applicant on Aug. 3, 2011 for U.S. Appl. No. 11/867,630, filed Oct. 4, 2007 (Inventor—Baxter et al.; pp. 1-14).
Non-Final Office Action issued by USPTO on May 3, 2011 for U.S. Appl. No. 11/867,630, filed Oct. 4, 2007 (Inventor—Baxter et al.; pp. 1-7).
Notification of Grant issued on Nov. 1, 2011 for GB Pat. App. No. 0907552.4, national phase of Intl. App. No. PCT/US2007/080497, filed Oct. 4, 2007 (Inventor—Baxter et al.; Applicant—MMJ Labs, LLC; pp. 1-2).
Response to Examination Report filed on Oct. 19, 2011 for GB Pat. App. No. 0907552.4, national phase of Intl. App. No. PCT/US2007/080497, filed Oct. 4, 2007 (Inventor—Baxter et al.; Applicant—MMJ Labs, LLC; pp. 1-27).
Examination Report issued on Oct. 13, 2011 for GB Pat. App. No. 0907552.4, national phase of Intl. App. No. PCT/US2007/080497, filed Oct. 4, 2007 (Inventor—Baxter et al.; Applicant—MMJ Labs, LLC; pp. 1-2).
Response to Examination Report filed on Sep. 16, 2011 for GB Pat. App. No. 0907552.4, national phase of Intl. App. No. PCT/US2007/080497, filed Oct. 4, 2007 (Inventor—Baxter et al.; Applicant—MMJ Labs, LLC; pp. 1-16).
Examination Report issued on Jul. 25, 2011 for GB Pat. App. No. 0907552.4, national phase of Intl. App. No. PCT/US2007/080497, filed Oct. 4, 2007 (Inventor—Baxter et al.; Applicant—MMJ Labs, LLC; pp. 1-3).
Response to Examination Report filed on Jun. 24, 2011 for GB Pat. App. No. 0907552.4, national phase of Intl. App. No. PCT/US2007/080497, filed Oct. 4, 2007 (Inventor—Baxter et al.; Applicant—MMJ Labs, LLC; pp. 1-5).
Examination Report issued on Apr. 27, 2011 for GB Pat. App. No. 0907552.4, national phase of Intl. App. No. PCT/US2007/080497, filed Oct. 4, 2007 (Inventor—Baxter et al.; Applicant—MMJ Labs, LLC; pp. 1-2).
Response to Examination Report filed on Feb. 25, 2011 for GB Pat. App. No. 0907552.4, national phase of Intl. App. No. PCT/US2007/080497, filed Oct. 4, 2007 (Inventor—Baxter et al.; Applicant—MMJ Labs, LLC; pp. 1-23).
Examination Report issued on Oct. 26, 2010 for for GB Pat. App. No. 0907552.4, national phase of Intl. App. No. PCT/US2007/080497, filed Oct. 4, 2007 (Inventor—Baxter et al.; Applicant—MMJ Labs, LLC; pp. 1-3).
International Preliminary Report on Patentabillity issued on Apr. 7, 2009 by International Bureau of WIPO on for Intl. App. No. PCT/US2007/080497, filed on Oct. 1, 2010 (Inventor—Baxter et al.; Applicant—MMJ Labs, LLC; pp. 1-6).
Lenz, F.A. et al., "Painful Stimuli Evoke Potentials Recorded Over the Human Anterior Cingulate Gyrus," J. Neurophysiol, 79: 2231-2234, 1998.
Cohen, L.L. and Baxter, A.L., "Distraction Techniques for Procedural Pain in Children," Clinical Review, Medscape Pediatrics, Nov. 2008, pp. 1-18. http://cme.medscape.com/viewprogram/17791.
Allsup et al.; Difficulties of recruitment for a randomized controlled trial involving influenza vaccination in healthy older people; Gerontology; 2002; 48(3):170-173.
Chen et al.; Topical anesthetics in children: agents and techniques that equally comfort patients, parents, and clinicians; Curr Opin Pediatr; 2001; 13(4):324-330.
Cohen et al.; Comparative study of distraction versus topical anesthesia for pediatric pain management during immunizations; Health Psychol; 1999; 18(6):591-598.
Cummings et al.; Prevalence and source of pain in pediatric inpatients; Pain; 1996; 68(1):25-31.
Eichenfield et al.; A clinical study to evaluate the efficacy of ELA-Max (4% liposomal lidocaine) as compared with eutectic mixture of . . . ; Pediatrics; 2002; 109(6):1093-1099.
Luhmann et al.; A comparison of buffered lidocaine versus ELA-Max before peripheral intravenous catheter insertions in children; Pediatrics; 2004; 113(3 Pt 1):217-220.
Palmon et al.; The effect of needle gauge and lidocaine pH on pain during intradermal injection; Anesth Analg; Feb. 1998; 86(2):379-381.
Ramsook et al.; Efficacy of ethyl chloride as a local anesthetic for venipuncture and intravenous cannula insertion in a pediatric . . . ; Pediatr Emerg Care; 2001; 17(5):341-343.
Sinha et al.; Reducing venipuncture pain by cough trick; Anesth Analg; 2004; 99(3):952-953 (author reply 953).
Smith et al.; Vibration anesthesia: a noninvasive method of reducing discomfort prior to dermatologic procedures; Dermatology Online Journal; 2004; 10(2):1.
Spielberg et al.; Overcoming barriers to HIV testing: preferences for new strategies among clients of a needle exchange, . . . ; J Acquir Immune Defic Syndr; 2003; 32(3):318-327.
Taddio et al.; Effect of neonatal circumcision on pain response during subsequent routine vaccination; Lancet; 1997; 349(9052):599-603.
Wong et al.; Willingness to donate blood samples for genetic research: a survey from a community in Singapore; Clin Genet; 2004; 65(1):45-51.
Saijo et al.; Lack of pain reduction by a vibrating local anesthetic attachment: a pilot study; Anesth Prog; 2005; 52 (2):62-64.
Search Report and Written Opinion for International Patent Application No. PCT/US2007/080497; Apr. 2, 2008.

* cited by examiner

DEVICE AND METHOD FOR THE REDUCTION OF PAIN ASSOCIATED WITH NEEDLE STICKS

CROSS-REFERENCE TO RELATED APPLICATIONS

This application is a continuation of U.S. application Ser. No. 11/538,718 filed Oct. 4, 2006, which is herein incorporated in its entirety by this reference.

BACKGROUND OF THE INVENTION

1. Technical Field

The present invention generally relates to devices and methods for the reduction of the pain associated with needle sticks, including venipuncture and injection as well as the application of other sharps to the body. The present invention more specifically relates to a device using vibration or a combination of vibration and cold that is applied to a patient prior to and/or during the application of a needle or other sharp to the patient for the reduction of the pain associated with the application of the needle, methods for using the device, and methods for using vibration or a combination of vibration and cold for the reduction of the pain associated with the application of the needle.

2. Prior Art

According to many children, needle sticks are the most painful procedure performed in the hospital. The effects of untreated pain are remembered even by children too young to talk. Fear of needles and immunizations affect childrens' other healthcare experiences and parents' willingness to have them immunized. Needle phobia does not end in childhood. Geriatric patients cite it as a reason not to get a flu shot. Human immunodeficiency virus (HIV) patients say it is a reason for delaying being tested. The avoidance of obtaining dental care due to needle phobia is legendary.

Needle phobia is not isolated to the United States. In a survey asking for a blood sample for a study, 38% of adults in Singapore cited fear of needles and injections as their reason not to participate. Adolescents in Norway delayed or would not seek medical treatment due to fear of needle pain.

Effective means to decrease needle pain include local analgesia, distracting the patient, and confusing the nerves. Topical analgesics can reduce or eliminate needle pain, but cost between US$12 and US$150 per patient use. In addition, topical analgesics require prolonged application times or can cause vasoconstriction decreasing venipuncture success. Several devices either deliver lidocaine over 10 minutes using either electrical current (iontophoresis) or ultrasound, but the cost for these starts at US$50 per delivery.

The nerve fibers that transmit pain also transmit cold and vibration senses. Cold spray has been used at the site of a needle stick, but this actually increases distress in small children and causes vasoconstriction. Vibration has long been used to decrease the pain of dental injections, but vibrating needles have not been found to be effective in other dermal situations. Use of a simple hand-held vibrating massager has decreased injection pain in adults, but has been used alone without the adjuvant of cold therapy and has not been tested in children.

The related art devices generally are designed to be used at the site of the needle pain, rather than several centimeters proximal to the site. Further, none of the related devices incorporates the application of cold. Applying cold or vibration at the site, or immediately proximal to the site, can create logistical problems for the medical practitioner, and can cause a heightened anxiety in the patient, by requiring a plurality of devices to be located in a single location. Thus, such devices have a disadvantage.

Therefore, there is a need for an intentional agent (device and/or method) to decrease the pain of immunization, infiltration, injection and venipuncture, which would include both cold and vibration stimulation. Such a device should be reusable, easy to clean, tolerable to children and adults, and should incorporate a method to be adapted for use in the developing world (for example, operation with a power cord, with a battery, with a solar or light cell, or without the need for external power). As distraction also is an effective method for decreasing pain in children and adults, embodiments that include bright colors, ornamental designs, or simple tasks also are contemplated.

Accordingly, there is a need for a device method that allows for the reduction of the pain associated with hypodermic needle sticks. There also is a need for a device and method using vibration or a combination of vibration and cold that is applied to a patient prior to and/or during the application of a hypodermic needle to the patient for the reduction of the pain associated with the application of the hypodermic needle. It is to these needs and others that the present invention is directed.

BRIEF SUMMARY OF THE INVENTION

Briefly, the invention is a device that is used to reduce the pain of a needle stick to a person. The invention generally comprises a casing containing a vibratory device and a temperature reducing device. The means for vibratory device can be any of the known vibratory devices such as for illustrative purposes personal vibratory devices scaled down to a size that can fit in the casing and other vibratory motors of reduced size. The temperature reducing device, hereinafter termed a cold source, can be any of the known devices such as for illustrative purposes cold packs, cold gel pack, metal ingots, and ice or other frozen compounds.

An exemplary embodiment of the device comprises a casing housing the various components of the invention and an optional strap for holding the device to the patient. The casing preferably is manufactured of a more flexible or pliant material in the form of an enclosed structure. The casing can be any shape, and preferably is in the shape of a three-dimensional polygon (for use with an adult use) or an animal or other distractive shape (for use with a child). Any other shape may be employed, so long as the shape is large enough and structured so as to be able to contain the various working components of the invention.

The device is applied externally to the skin surface of a patient to whom a hypodermic needle or other type of needle or pointed or pain producing object is being applied. The positioning of the device on the skin surface of the patient necessarily is between the needle prick site and the nerve plexi between the needle stick site and the spinal cord or brain, along the nerve path, as this will have the greatest analgesic effect. However, the device may be positioned at any point generally proximal to the needle stick site.

A minimal embodiment of the features of the invention comprises a casing having means for containing or holding a vibrational source and a thermal source, and an on/off switch for the vibrational source. An optional strap can be used to hold the device on to the patient, for example a strap that extends around a limb of the patient to secure the device on the limb of the patient such that the medical practitioner need not have an assistant present to hold the device, or such that the medical practitioner can have both hands free to treat the patient. Further, the strap can act as a tourniquet, if necessary.

Alternatively, the device can be held against the patient by the practitioner, the practitioner's assistant, or the patient.

The casing has an application area that comprises a thermal area and a vibrational area. A thermal source cooperates with the thermal area to apply cold to the patient, and a vibrational source cooperates with the vibrational area to apply vibration to the patient. The placement of the thermal source is variable so long as the cooling effects of the thermal source can be felt on the patient so as to produce thermal analgesia. The placement of the vibrational source is variable so long as the vibrational effects of the vibrational source can be felt on the patient so as to produce vibrational analgesia. The casing is a generally hollow structure sized to contain the thermal source and the vibrational source.

The thermal source can be any conventional thermal source capable of storing and transferring cold, such as metal ingots, low freezing point (below 45° F. or 7.2° C.) liquids and gels, ceramics, polymers, other heat sinks, and even ice. The vibrational source can be any conventional vibrational source or means for producing vibrations. The on/off switch can be a common switch and is used to turn the vibrational source on and off, namely to start and stop the vibration, respectively. The power source for operating the vibrational source can be any type of power source such as but not limited to a connection to an alternating current source (a wall plug), a solar or other light cell, a miniature reactor, a mechanical source such as a flywheel or springs, or the like.

In operation and use, the device helps to counter pain through the use of vibrational and thermal analgesia. More specifically, the invention is a device for concurrently (contemporaneously) applying a combination of vibrational analgesia and thermal analgesia to a patient proximal to the site, generally within 2.5 cm to 15 cm of the site. It is known that vibration helps to reduce pain as the vibrational, or motion, nerves surmount the pain nerves, which is known as gate theory to those of ordinary skill in the field. Similarly, it is known that cold helps to reduce pain as the temperature nerves surmount the pain nerves. It also is known that both vibrational and thermal analgesia are more effective when applied generally between the pain source and the brain, and more specifically close to the nerve plexi where the various nerve types (pain, temperature and motion) converge in the body.

The thermal source is cooled, if necessary to within a predetermined temperature range. The thermal source then is placed within the casing.

Alternatively, if the device is made to certain standards, the entire device already containing the thermal source can be cooled to the desired temperature. After a doctor or other medical practitioner has determined where on the patient's body a needle stick will occur, the device is applied to the body at a location between the needle stick site and the patient's brain, and more specifically is placed between the needle stick site and the patient's most proximal joint.

The device with the thermal source is applied to the selected area of the patient such that a thermal area and a vibrational area contact the patient's skin. The thermal source is allowed to act upon the patient for a time necessary to initiate thermal analgesia, which can be for a period of seconds up to a period of several minutes or more, but preferably is for between 0 and 60 seconds, and more preferably between 10 and 60 seconds. Once suitable thermal analgesia is achieved, or concurrently when the thermal source is applied to the patient, the vibrational source is actuated by the on/off switch, creating vibration. The vibrational source also is allowed to act upon the patient for a time necessary to initiate vibrational analgesia, which can be for a period of seconds up to a period of several minutes or more, but preferably is for between 0 and 60 seconds, and more preferably between 5 and 30 seconds, and even more preferably between 5 and 10 seconds. After thermal analgesia and vibrational analgesia are initiated, the medical practitioner can apply the needle to the patient.

After the needle has been applied to and removed from the patient, the device can be removed and/or the thermal source can be removed from acting on the patient and/or the vibrational source can be turned off. However, it is possible to leave the device, including the active thermal source and the active vibrational source in contact with the patient for a period of between 0 and 60 seconds to continue to reduce any pain associated with the needle stick.

These features, and other features and advantages of the present invention will become more apparent to those of ordinary skill in the relevant art when the following detailed description of the preferred embodiments is read in conjunction with the appended drawings in which like reference numerals represent like components throughout the several views. The figures and the detailed description which follow more particularly exemplify these and other embodiments of the invention.

DETAILED DESCRIPTION OF THE PREFERRED EMBODIMENTS

Figure 1:
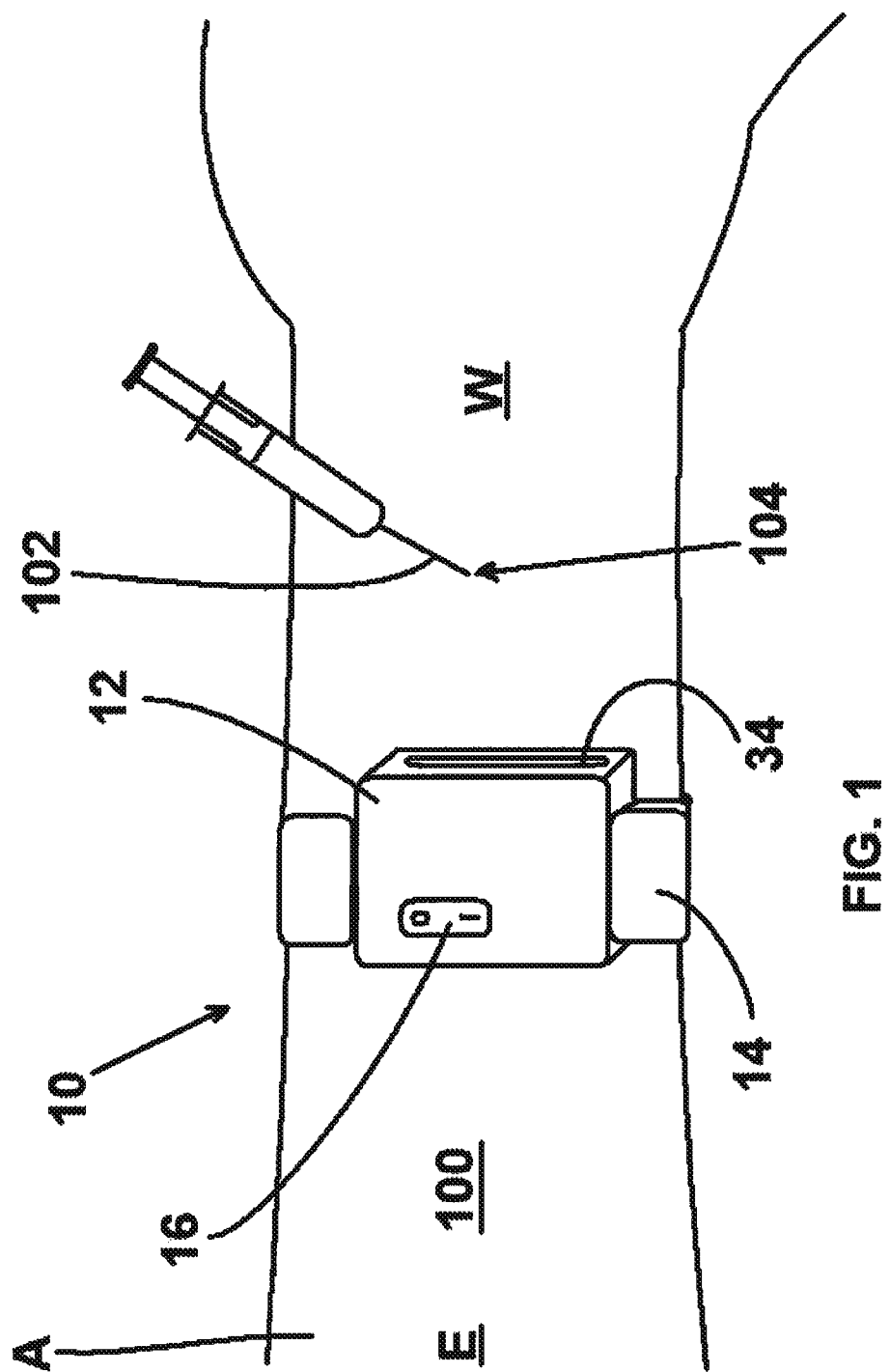
FIG. 1 is a perspective view of an embodiment of the invention.
Figure 2:
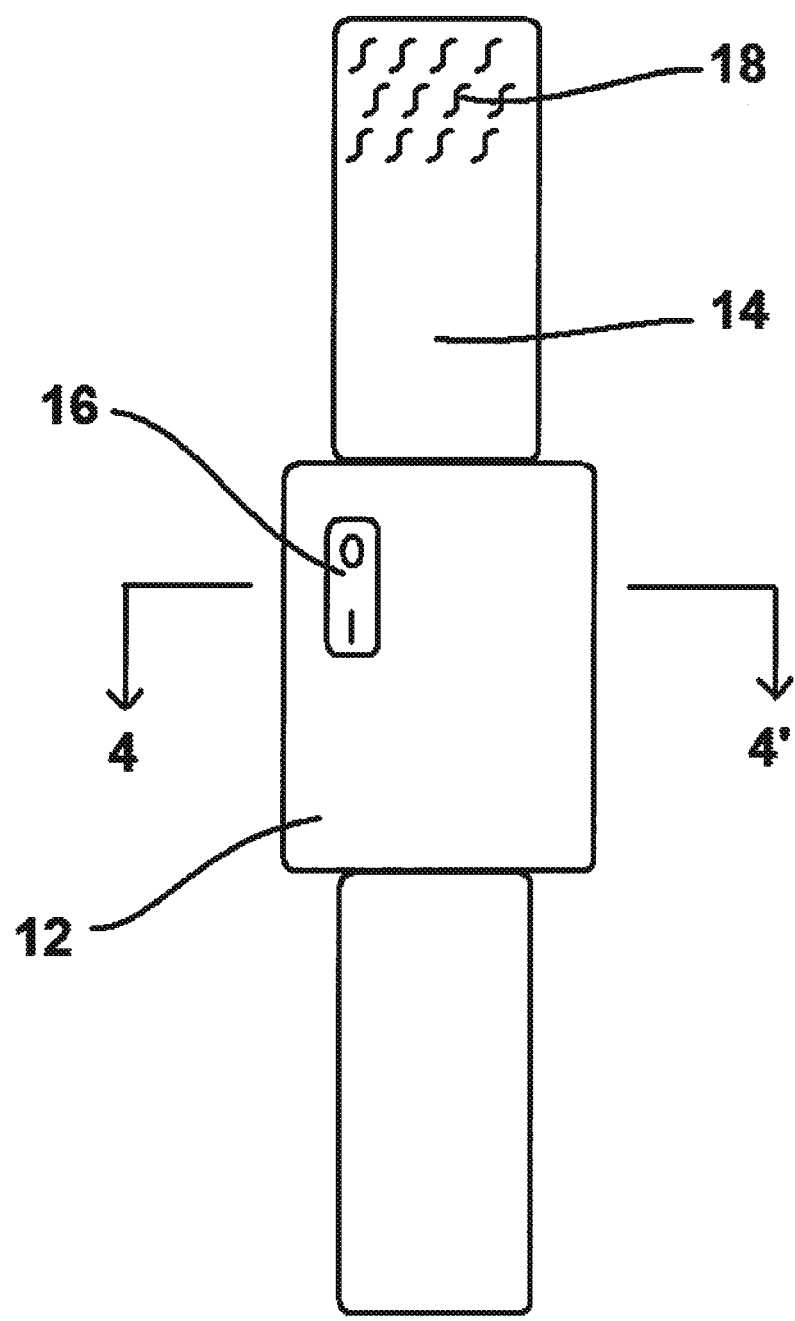
FIG. 2 is a top view of an embodiment of the invention with both vibration and cold capabilities.
Figure 3:
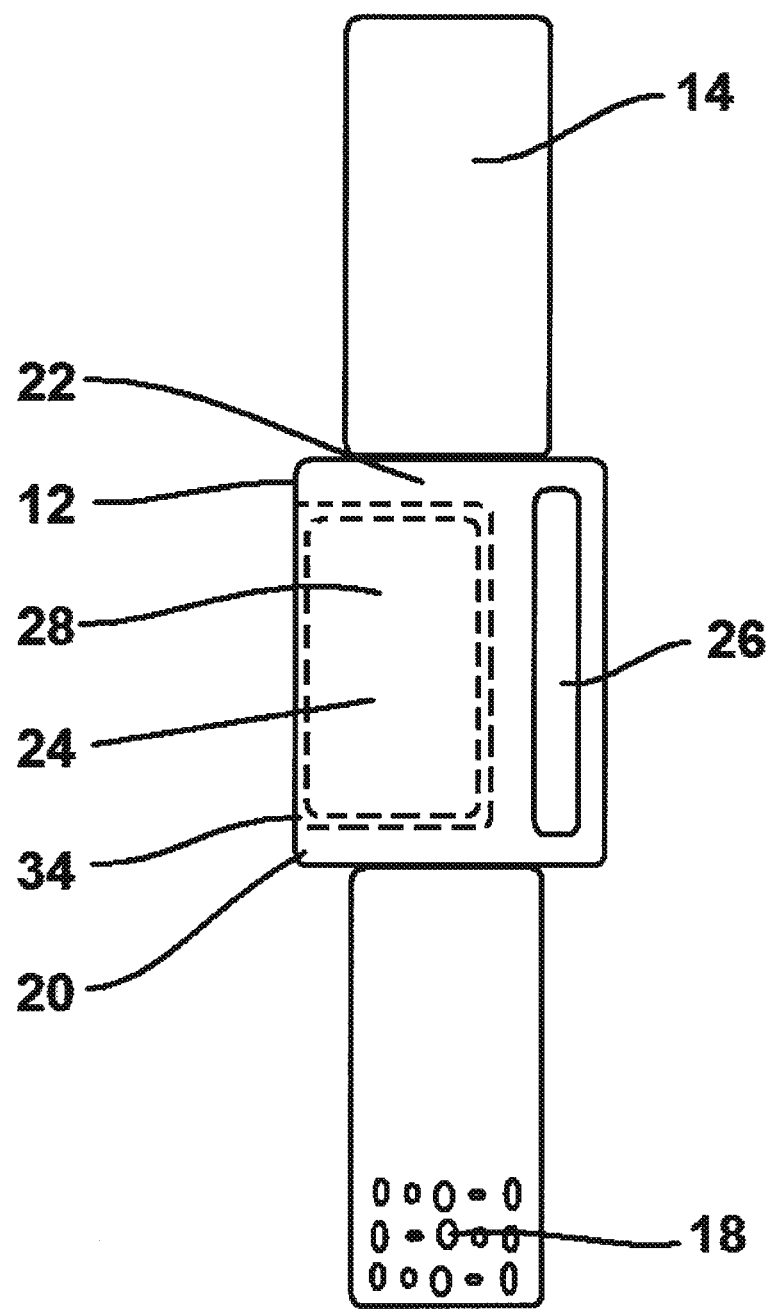
FIG. 3 is a bottom view of an embodiment of the invention with both vibration and cold capabilities.
Figure 4:
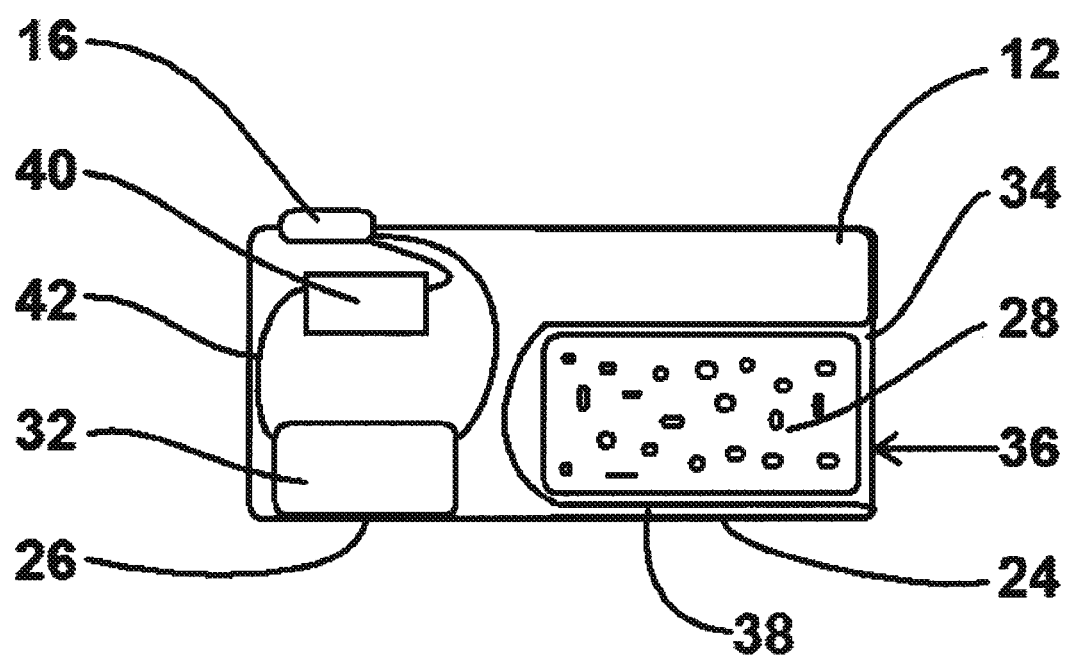
FIG. 4 is sectional side view of the embodiment of the invention as shown along line 4-4' of FIG. 2.
Figure 5:
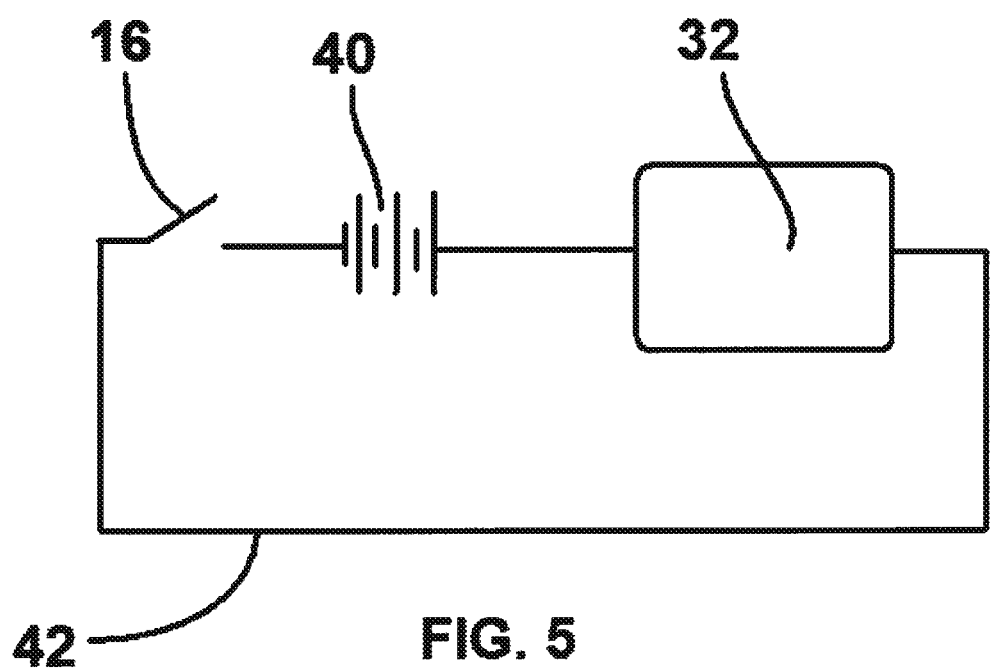
FIG. 5 is a circuit diagram of an embodiment of the invention.
Figure 6:
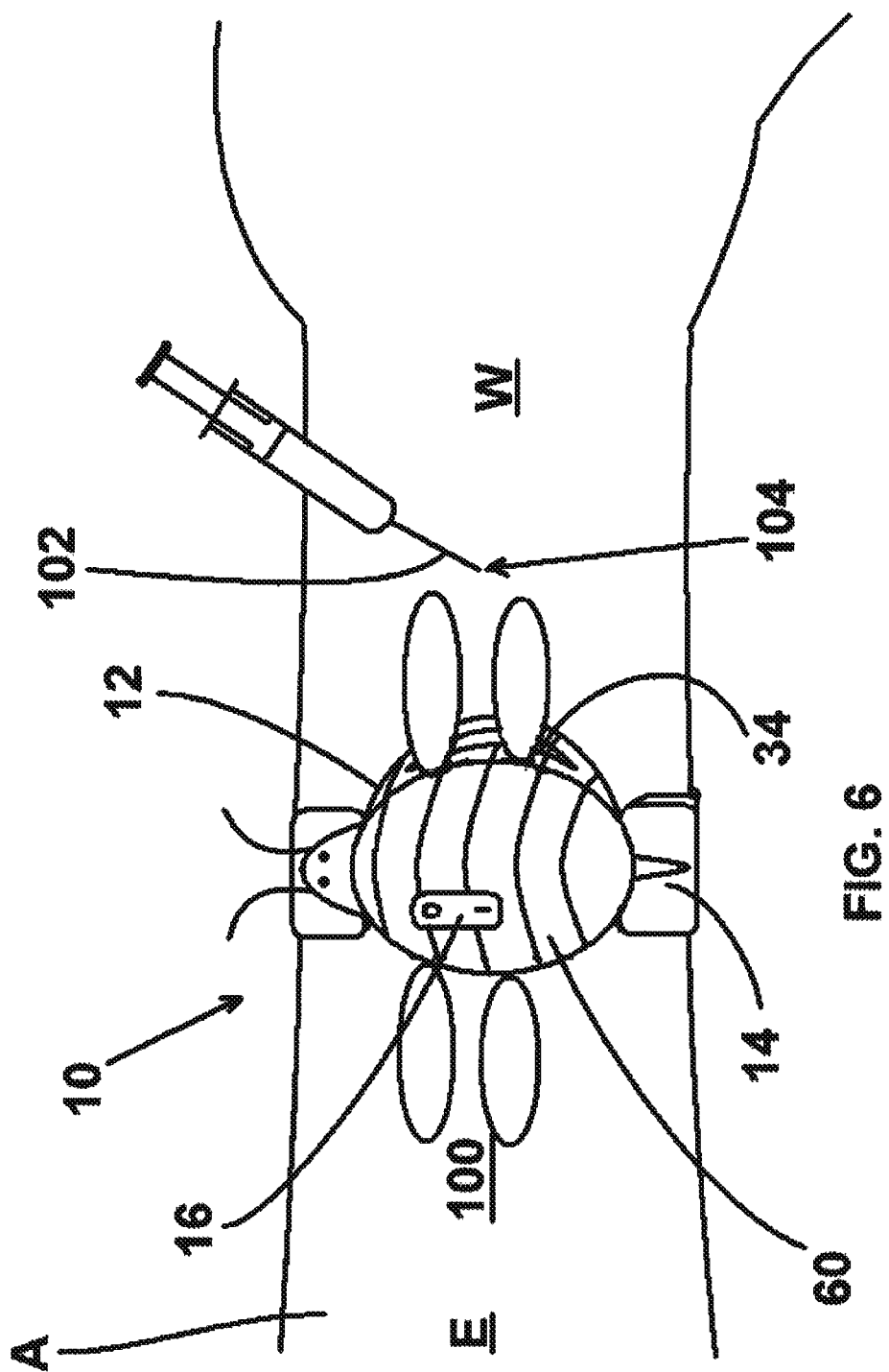
FIG. 6 is a perspective view of an embodiment of the invention having an ornamental cover or casing.

Preferred and alternative embodiments of the invention now will be disclosed in conjunction with the appended figures. FIG. 1 is a perspective view of an embodiment of the invention. FIG. 2 is a top view of an embodiment of the invention with both vibration and cold capabilities. FIG. 3 is a bottom view of an embodiment of the invention with both vibration and cold capabilities. FIG. 4 is sectional side view of the embodiment of the invention as shown along line 4-4' of FIG. 2. FIG. 5 is a circuit diagram of an embodiment of the invention. FIG. 6 is a perspective view of an embodiment of the invention having an ornamental cover or casing that can act as an additional distraction to the patient.

"Hypodermic needles" as used herein includes, but is not limited to, all different types of needles, pins, probes, sharps and the like that can be used to inject, remove, or apply fluids, medications and the like to a patient, as well as to conduct tests such as but not limited to allergy tests to a patient.

"Thermal analgesia" as used herein includes, but is not limited to, the use or application of cold or reduced temperature (or the removal of heat) to a patient to induce an analgesic effect.

"Vibrational analgesia" as used herein includes, but is not limited to, the use or application of vibration to a patient to induce an analgesic effect.

"Vibrational and thermal analgesia" as used herein includes, but is not limit to, the use or application of both cold or reduced temperature (or the removal of heat) concurrently, substantially concurrently, or sequentially with the use or application of vibration to a patient to induce an analgesic effect.

Referring now to FIG. 1, a perspective view of an embodiment of the device 10 invention is shown as applied to the arm A of a patient, showing the casing 12 housing the various components of the invention and an optional strap 14 for holding the device 10 to the patient. The casing 12 preferably is manufactured of a flexible or pliant material, such as for illustrative purposes a natural or synthetic woven or non-woven fabric, a rubber or other flexible polymer material, or a silicone-based material, to provide an enclosed structure. Other flexible or pliant or other materials may be employed, and it is preferred that the material of construction is non-toxic, hypo-allergenic and non-staining to the patient.

The casing 10 can be any shape, and preferably is in the shape of a three-dimensional polygon (for use with an adult use) or an animal or other distractive shape (for use with a child) and having a hollow interior or interior sections for containing the operating elements of the invention. Any other shape (as used herein, the term shape is used in the broad sense of three-dimensional works) may be employed, so long as the shape is large enough and structured so as to be able to contain the various working components of the invention as more fully disclosed below.

The device is shown in FIG. 1 applied to the arm 100 of a patient to whom a hypodermic needle 102 is being applied. As disclosed in more detail below, the positioning of the device 10 on the patient is between the needle prick site 104 and a nerve plexi (not shown, but the location of which is known t those of ordinary skill in the pain alleviation field) between the needle stick site 104 and the spinal cord or brain, in this example at or proximal to the elbow E. Thus, in FIG. 1, the device 10 is place farther up the arm 100 of the patient from the needle prick site 104, which, in the placement of the needle stick site 104 in FIG. 1, is closer to the elbow E than to the wrist W. Preferably, the device 10 is placed approximately 2.5 cm to 15 cm from the needle prick site 104.

Referring now to FIG. 2, a top view of an embodiment of the invention is shown. A minimal embodiment of the external features of the invention comprises the casing 12 and an on/off switch 16. Optional strap 14 can be used to hold the device 10 on to the patient. Alternatively, the device 10 can be held against the patient by the practitioner, the practitioner's assistant, or the patient. Strap 14 can be attached to the casing 12 in any conventional manner or can be an extension of casing 12 itself. For example, strap 14 and casing 12 can be attached together much like a conventional watch and watch-band with hinges or pins. For another example, strap 14 can be an extension of the fabric or other material of casing 12. The ends of strap 14 preferably have some type of connecting device, such as a hook and loop fastener 18, a clasp, a clip, snaps, magnets, or the like for attaching the device about the patient's body part. Alternatively, if the ends of strap 14 are flexible, the ends can be tied together around the patient's body part.

Referring now to FIG. 3, a bottom view of an embodiment of the invention is shown. The casing 12 has a peripheral bottom rim 20 that defines an application area generally designated 22 in FIG. 3. Application area 22 comprises thermal area 24 and vibration area 26. Although thermal area 24 and vibration area 26 area shown as discrete areas in FIG. 3, this is for illustrative purposes only, as there need not be any physical delineation between thermal area 24 and vibration area 26 and application area 22. As disclosed in more detail below, thermal source 28 cooperates with thermal area 24 to apply cold to the patient, and vibrational source 32 cooperates with vibration area 26 to apply vibration to the patient. Thermal area 24 and vibrational area 26 can coextent.

Thermal source pocket 34 is a slot, fold or other type of compartment in casing 12 into which thermal source 28 can be placed. As shown in FIG. 3, thermal source pocket 34 is accessed on the side of the casing 12 via a mouth 36. Alternatively, mouth 36 can be located at other locations on casing 12 depending on the size and shape of casing 12 and the location of the vibrational source 32 within the casing 12. Alternatively, thermal source 28 can be contained within the main housing volume of casing 12. Thus, the placement of thermal source 28 is variable so long as the cooling effects of thermal source 28 can be felt on the patient so as to produce thermal analgesia. Thermal area 24 in its simplest form is an area on the application area 22 on the device 10 that allows the thermal effects (cold) from thermal source 28 to contact the patient.

Vibration area 26 is a pad or other area on casing 12 in vibratory contact with vibrational source 32. As disclosed in more detail below, vibrational source 32 preferably is contained within the main housing volume of casing 12. The placement of vibrational source 32 is variable so long as the vibration effects of vibrational source 32 can be felt on the patient so as to produce vibrational analgesia. As shown in FIG. 3, vibrational area 26 is proximal to thermal area 24; however, vibrational area 26 can coextend with thermal area 24. Vibrational area 26 in its simplest form is an area on the application area 22 on the device 10 that allows the vibrations from vibrational source 32 to contact the patient.

Referring now to FIG. 4, a sectional side view of the embodiment of the invention as shown along line 4-4' of FIG. 2 is shown. Casing 12 is a generally hollow structure sized to contain thermal source 28 and vibrational source 32. More specifically, casing 12 can be a rigid hollow case having an interior volume or a flexible or pliant case having an interior volume. Such cases are known, as well as their materials and methods of construction. It is only important that casing 12 be constructed such that casing can contain and hold thermal source 28 and vibrational source 32 in a predetermined position relative to the patient when the invention is applied to the patient.

As shown illustratively in FIG. 4, thermal source 28 is contained in thermal source pocket 34. Thermal source 28 can be placed within thermal source pocket through mouth or opening 36 and can be held within thermal source pocket 34 by friction, adhesives, fasteners, or by a zipper or other type of closure on mouth or opening 36. It is preferable that the bottom wall 38 of thermal source pocket 34 be sufficiently thin or have sufficient thermal transfer characteristics so as to allow the efficient transfer of cold from thermal source 28 to the patient.

Thermal source 28 can be any conventional thermal source capable of storing and transferring cold (removing heat). Illustrative examples of suitable thermal sources 28 include metal ingots, low freezing point (below about 45° F. or 7.2° C.) liquids and gels, ceramics, polymers, other heat sinks, and even ice. Such thermal sources 28 are known. It is only important that thermal source 28 be able to transfer cold to the patient in a sufficient amount so as to produce thermal analgesia. For example, providing a temperature of below about 45° F. or 7.2° C., and preferably between about 28° F. or −2.2° C. and about 54° F. or 12.2° C., and more preferably between about 38° F. or 3.3° C. and about 45° F. or 7.2° C., to the patient prior to and during the needle stick is sufficient to provide a suitable level of thermal analgesia. The thermal source 28 is applied to the patient for a time period sufficient to initiate thermal analgesia, which can be between 0 seconds and several minutes or more depending on the patient. However, it is preferable to apply the thermal source 28 to the patient for a period of about 0 to 60 seconds, and preferably between about 10 second and about 60 seconds, prior to the needle stick and continuing during the needle stick to provide a suitable level of thermal analgesia.

As shown illustratively in FIG. 4, vibrational source 32 is contained within the interior of casing 12. Vibrational source 28 can be placed within casing 12 during manufacture or, if casing 12 has an ingress and egress means, such as a zipper or other closure, at any time after manufacture. An ingress and egress means is preferred, as one embodiment of vibrational source 32 utilizes a battery as the power source 40, and it may be necessary to change the battery on occasion. Vibrational source 28 and power source 40 can be held within casing 12 by friction, adhesives, fasteners, or other types of securing means. Alternatively, the interior volume of casing 12 can be approximately the same dimensions as the vibrational source 28, including the power source 40, such that additional means for securing the vibrational source 28 are unnecessary. It is preferable that the bottom wall 38 of casing proximal to vibrational source 32 be sufficiently thin or have sufficient vibrational transfer characteristics so as to allow the efficient transfer of vibration from vibrational source 28 to the patient.

Vibrational source 32 can be any conventional vibrational source or means for producing vibrations. As shown in FIG. 4, vibrational source 32 further comprises a power source 40 and wiring 42 electrically connecting vibrational source 32 and power source 40 to on/off switch 16. Illustrative examples of suitable vibrational sources 32 include elliptical flywheel motors, eccentric motors, and the like. Such vibrational sources 32 are known. It is only important that vibrational source 32 be able to transfer vibration to the patient at a sufficient level to produce vibrational analgesia. For example, providing vibrations of between about 300 vibrations per minute and about 9000 vibrations per minute, preferably between about 3700 vibrations per minute and about 6000 vibrations per minute, and more preferably between about 4400 vibrations per minute and about 5800 vibrations per minute, to the patient prior to and during the needle stick is sufficient to provide a suitable level of vibrational analgesia. The vibrational source 32 is applied to the patient for a time period sufficient to initiate vibrational analgesia, which can be between 0 seconds and several minutes or more depending on the patient. However, it is preferable to apply the vibrational source 32 to the patient for a period of about 0 seconds to about 60 seconds, preferably between about 5 seconds and about 30 seconds, and more preferably between about 5 seconds and about 10 seconds prior to the needle stick, and continuing during the needle stick to provide a suitable level of vibrational analgesia.

Vibrational source 32 can produce a single vibrational cycle, multiple vibrational cycles, or be variable. In other words, vibrational source 32 can be a vibrational motor that operates at, for example, 4700 vibrations per minute or, for another example, at 5700 vibrations per minute. Alternatively, vibrational source 32 can be a vibrational motor that operates at two or more vibrational cycles, for example, 4700 vibrations per minute and 5700 vibrations per minute, and can be switched between vibrational cycles by a switch or other mechanism. Alternatively, vibrational source 32 can be a vibrational motor that operates at many different vibrational cycles along a continuum by using a potentiostatic switch, for example, vibrational source 32 can be varied continuously or step-wise between 3000 vibrations per minute and 6000 vibrations per minute.

Switch 16 can be a common switch and is used to turn vibrational source 32 on and off, namely to start and stop the vibration, respectively. Switch 16 can be secured to casing 12 at any convenient position where it may readily be actuated. Switch 16 is electrically connected in a known manner between the power source 40 and the vibrational source 32 to control the application of power to the vibrational source 32. Thus, when the vibrational source 32 is switched on, the vibrating force produced from the vibrational source, such as the various types of motors disclosed above, will be transmitted through the casing 12 to apply on the body of the patient.

Switch 16 can be a common on/off switch, such as a toggle, lever, push-button, capacitance or other switch. This type of switch 16 would be practical with a single vibrational cycle motor. Alternatively, switch 16 can be a common three-way switch. This type of switch 16 would be practical with a double vibrational cycle motor. Alternatively, switch 16 can be a common potentiostat. This type of switch 16 would be practical with a vibrational motor that operates at many different vibrational cycles along a continuum.

Referring now to FIG. 5, a representative circuit diagram for the vibrational source 32 is shown. Vibrational source 32, power source 40 and on/off switch 16 are electrically connected in series by wiring 42. Power source 40 is illustrated in FIG. 5 as a battery; however, power source 40 can be any type of power sources such as but not limited to a connection to an alternating current source (a wall plug), a solar or other light cell, a reactor, a mechanical source such as a flywheel or springs, or the like. It is only important that power source 40 be able to provide sufficient power to vibrational source 32 so as to produce sufficient vibration for effecting vibrational analgesia.

In operation and use, the device helps to counter infiltration pain through the use of vibrational and thermal analgesia. According to known gate theory, vibration helps to reduce pain as the vibrational, or motion, nerves surmount the pain nerves. Similarly, it is known that cold helps to reduce pain as the temperature nerves surmount the pain nerves. It also is known that vibrational and thermal analgesia is more effective when applied generally between the pain source and the brain, and more specifically close to the nerve plexi where the various nerve types (pain, temperature and motion) converge in the body, generally at or proximal to a joint.

The following example of use will describe a medical procedure as this is a preferred use for the device 10. However, it should be understood that the device can be used in many other situations where pain is to be reduced.

The thermal source 28 is cooled, if necessary. For example, if the thermal source 28 is a metal ingot or low freezing point gel, the thermal source 28 is placed in a refrigerator, freezer, or other cold site. When the thermal source 28 is of a satisfactory temperature, the thermal source 28 is placed within the casing 12, such as within the thermal source pocket 34. After a doctor or other medical practitioner has determined where on the patient's body a needle stick will occur, the device 10 is applied to the body at a location between the needle stick site 104 and the patient's brain, along the nerve path. In the example shown in FIG. 1, the needle stick site 104 is proximal to the patient's wrist W. Therefore, the device 10 generally is placed between the needle stick site 104 and the patient's brain, and more specifically in the illustrative example shown in FIG. 1, is placed between the needle stick site 104 and the patient's elbow E and proximal to the nerve plexi proximal to the elbow. For example, the placement of the device 10 generally is within about 2.5 cm to about 15 cm of the needle stick site 104, which range of location often will encompass the nerve plexi. Preferably, the needle stick site 104 can be selected so as to be within 15 cm of the closest nerve plexi.

The device 10 with the thermal source 28 is applied to the selected area of the patient such that the application area 22, comprising the thermal area 24 and the vibrational area 26, contact the patient's skin. The thermal source 28 is allowed to act upon the patient for a suitable time period so as to initiate thermal analgesia. Once suitable thermal analgesia is achieved, or concurrently when the thermal source is applied to the patient, the vibrational source 32 is actuated by the switch 16, creating vibration. The vibrational source 32 also is allowed to act upon the patient for a suitable time period so as to initiate vibrational analgesia. After thermal analgesia and vibrational analgesia are initiated, the medical practitioner can apply the needle 102 to the patient. The thermal source 28 and the vibrational source 32 are allowed to continue to act upon the patient during the needle stick activity.

After the needle 102 has been applied to and removed from the patient, the entire device 10 can be removed and/or just the thermal source 28 can be removed from the device 10 and therefore from acting on the patient, and/or the vibrational source 32 can be turned off and therefore from acting on the patient. However, the device 10, including the active thermal source 28 and the active vibrational source 32, can be left in contact with the patient after the needle stick activity has ended, for example in situations where needle stick pain persists, for a time period sufficient to maintain thermal and/or vibrational analgesia. In one illustrative method, the device 10 is left in contact with the patient for a period of between 0 and 60 seconds, preferably between 5 and 30 seconds, and more preferably between 5 and 10 seconds, to continue to reduce any pain associated with the needle stick.

Referring now to FIG. 6, alternative embodiments include casings 12 having interesting or distracting shapes. Distraction also is known to help reduce pain, especially to children. For example, the casing 12 could be a flexible material in the shape of a bumble bee, as illustrated in FIG. 6, or dinosaur. When the device 10 is applied to a child, the distracting shape both can lessen the fear a child may have to the device 10 and help to decrease the subsequent pain of the needle stick.

Thus, in one of its simplest forms, the invention is a device for reducing the pain associated with a needle stick, comprising:

a) a casing comprising an application area, at least a portion of the application area constructed to contact a subject's skin;

b) a thermal source contained within the casing, the thermal source capable of being cooled; and c) a vibrational source contained within the casing, the vibrational source capable of producing vibration, wherein the application area is constructed to allow the transmission of cold from the thermal source to the subject's skin and the transmission of the vibration from the vibrational source to the subject's skin, whereby the combination of the transmission of cold and vibration produces a thermal analgesia and vibrational analgesia effect on the patient so as to reduce the pain associated with a needle stick.

Further, in one of its simples forms, the invention is a method for reducing the pain associated with a needle stick, comprising the steps of:

a) providing a device comprising a casing having an application area, at least a portion of the application area constructed to contact a subject's skin;

b) providing a thermal source contained within the casing, the thermal source capable of being cooled, and cooling the thermal source;

c) providing a vibrational source contained within the casing, the vibrational source capable of producing vibration;

d) contacting the application area to the subject's skin;

e) activating the vibrational source so that the vibrational source produces vibrations; and f) maintaining the thermal source and the vibrational source on the patient's skin for a time period prior to and during the application of a needle to the patient's skin, wherein the application area is constructed to allow the transmission of cold from the thermal source to the subject's skin and the transmission of the vibration from the vibrational source to the subject's skin, whereby after contacting the application area to the subject's skin and activating the vibrational sources, cold and vibration is transmitted to the subject via the application area, whereby the combination of the transmission of cold and vibration produces a thermal analgesia and vibrational analgesia effect on the subject so as to reduce the pain associated with a needle stick.

The invention further comprises the use of removable and interchangeable covers and casings, such as different animal shapes and various colors, textures and the like, such that the device can be changed to please the patient. For example, while a young child may prefer or be better distracted by a green dinosaur shaped casing, and adult may not care and a plain blue casing would be sufficient.

The above detailed description of the preferred embodiments, and the examples, are for illustrative purposes only and are not intended to limit the scope and spirit of the invention, and its equivalents, as defined by the appended claims. One skilled in the art will recognize that many variations can be made to the invention disclosed in this specification without departing from the scope and spirit of the invention.

What is claimed is:

1. A device for reducing acute pain in a subject, comprising:

a) a casing comprising an application area;

b) a vibrational source contained within the casing, the vibrational source capable of producing vibration;

c) a switch secured to the casing and in operative communication with the vibrational source for selectively activating the vibrational source; and d) a thermal source capable of being cooled;

wherein the application area is constructed to transmit vibration from the vibrational source to the subject's skin, wherein the thermal source is operatively positioned relative to the application area such that the thermal source and the application area cooperate to provide cold and vibration to the subject's skin, and wherein the combination of the cold and vibration produces a thermal analgesia and vibrational analgesia effect on the subject so as to reduce the acute pain in the subject.

2. The device of claim 1, wherein the casing is manufactured from a pliant material comprising natural or synthetic woven or non-woven fabrics, rubbers, flexible polymer materials, or flexible silicone-based materials.

3. The device of claim 1, wherein the casing is manufactured from a material that is non-toxic, hypo-allergenic and non-staining to the subject.

4. The device of claim 1, wherein the thermal source is capable of cooling the subject's skin to a temperature of below about 45° F. (7.2° C.).

5. The device of claim 1, wherein the thermal source is capable of cooling the subject's skin to a temperature of between about 54° F. (12.2° C.) and about 28° F. (−2.2° C.).

6. The device of claim 1, wherein the thermal source is capable of cooling the subject's skin to a temperature of between about 45° F. (7.2° C.) and about 38° F. (3.3° C.).

7. The device of claim 1, wherein the vibrational source is capable of imparting vibrations to the subject's skin at a rate of between about 300 vibrations per minute and about 9000 vibrations per minute.

8. The device of claim 1, wherein the vibrational source is capable of imparting vibrations to the subject's skin at a rate of between about 3700 vibrations per minute and about 6000 vibrations per minute.

9. The device of claim 1, wherein the vibrational source is capable of imparting vibrations to the subject's skin at a rate of between about 4400 vibrations per minute and about 5800 vibrations per minute.

10. The device of claim 1, further comprising a removable cover or casing.

11. The device of claim 1, wherein, during operation, the vibrational source is configured to be varied among a plurality of vibrational cycles.

12. A method for reducing acute pain in a subject, comprising,
 a) prior to a needle stick in a subject, providing a device comprising,
  a casing having an application area;
  a vibrational source contained within the casing, the vibrational source capable of producing vibration;
  a switch secured to the casing and in operative communication with the vibrational source;
 b) cooling a thermal source to a desired temperature;
 c) operatively positioning the cooled thermal source relative to the application area of the casing;
 d) placing the device on the subject such that the thermal source contacts the subject's skin at a desired location, the desired location being spaced a predetermined distance from an injection site on the subject's skin;
 e) activating the vibrational source using the switch; and
 f) maintaining the device at the desired location for a time period prior to and during the application of a needle to the injection site,
 wherein the application area is constructed to transmit vibration from the vibrational source,
 wherein the thermal source and the application area cooperate to provide cold and vibration to the subject's skin, and
 wherein the combination of the cold and vibration transmitted produces a thermal analgesia and vibrational analgesia effect on the subject so as to reduce the acute pain in the subject from a needle stick.

13. The method of claim 12, further comprising the step of cooling the subject's skin to a temperature of between about 54° F. (12.2° C.) and about 28° F. (−2.2° C.).

14. The method of claim 12, wherein the step of activating the vibrational source comprises imparting vibrations to the desired location on the subject's skin at a rate of between about 300 vibrations per minute and about 9000 vibrations per minute.

15. The method of claim 12, wherein the step of activating the vibrational source comprises imparting vibrations to the desired location on the subject's skin at a rate of between about 3700 vibrations per minute and about 6000 vibrations per minute.

16. The method of claim 12, wherein the step of activating the vibrational source comprises imparting vibrations to the desired location on the subject's skin at a rate of between about 4400 vibrations per minute and about 5800 vibrations per minute.

17. The method of claim 12, wherein the desired location on the subject's skin is positioned between the injection site and the subject's brain, along a nerve path of the subject.

18. The method of claim 12, wherein the desired location on the subject's skin is positioned proximal to a nerve plexi on the subject.

19. The method of claim 12, further comprising, contacting the device to the desired location on the subject's skin for a period of between about 0 second and about 60 seconds prior to the needle stick.

20. The method of claim 12, wherein the step of activating the vibrational source comprises varying the vibrational source among a plurality of vibrational cycles.

* * * * *